United States Patent
Ward

(10) Patent No.: US 7,214,674 B2
(45) Date of Patent: May 8, 2007

(54) HETEROCYCLYMETHYLPIPERIDINES AND -PIPERAZINES POSSESSING AFFINITY AT 5HT-1 TYPE RECEPTORS

(75) Inventor: Simon E Ward, Harlow (GB)

(73) Assignee: Glaxo Group Limited, Greenford, Middlesex (GB)

( * ) Notice: Subject to any disclaimer, the term of this patent is extended or adjusted under 35 U.S.C. 154(b) by 311 days.

(21) Appl. No.: 10/503,969

(22) PCT Filed: Feb. 17, 2003

(86) PCT No.: PCT/EP03/01708

§ 371 (c)(1),
(2), (4) Date: Aug. 9, 2004

(87) PCT Pub. No.: WO03/068771

PCT Pub. Date: Aug. 21, 2003

(65) Prior Publication Data

US 2005/0153974 A1   Jul. 14, 2005

(30) Foreign Application Priority Data

Feb. 18, 2002   (GB) .................. 0203811.5

(51) Int. Cl.
*C07D 413/06* (2006.01)
*C07D 413/14* (2006.01)
*A61K 31/496* (2006.01)
*A61K 31/538* (2006.01)

(52) U.S. Cl. .................. 514/230.5; 514/249; 514/314; 514/253.06; 514/266.22; 514/266.2; 544/105; 544/284; 544/353; 544/363

(58) Field of Classification Search ................ 544/105, 544/284, 353, 363; 546/152, 176; 514/249, 514/314, 230.5, 253.06, 266.22, 266.2
See application file for complete search history.

(56) References Cited

U.S. PATENT DOCUMENTS

2002/0019531 A1   2/2002   Kitazawa et al.

FOREIGN PATENT DOCUMENTS

| EP | 0 978 514 | 2/2000 |
| WO | WO 01 07434 | 2/2001 |
| WO | WO 01 07435 | 2/2001 |
| WO | WO 02 34754 | 5/2002 |
| WO | WO 02 36562 | 5/2002 |

*Primary Examiner*—Kahsay Habte
(74) *Attorney, Agent, or Firm*—Alyson W. Keating; Kathryn L. Sleburth; Mary E. McCarthy

(57) ABSTRACT

Compounds of formula (I) and pharmaceutically acceptable salts thereof are disclosed:

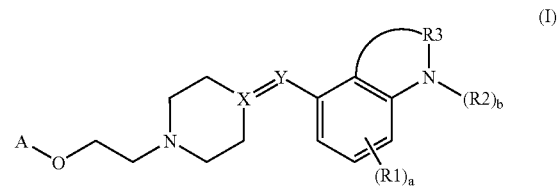

wherein: A is optionally substituted phenyl, naphthyl, indolyl, quinolinyl, quinazolinyl, indazolyl, isoquinolinyl or benzofuranyl; X is carbon, Y is CH and

═ is a double bond; or X is CH, Y is $CH_2$ or oxygen and

═ is a single bond; or X is nitrogen, Y is $CH_2$ and

═ is a single bond; R 1 is halogen, cyano, or $C_{1-6}$ alkoxy; a is 0,1, 2 or 3 ; b is 0 or 1 ; R 2 is hydrogen, $C_{1-6}$ alkyl, $C_{1-6}$ alkanoyl, fluoro$C_{1-6}$ alkanoyl, $C_{1-6}$ alkylsulfonyl, fluoro$C_{1-6}$ alkylsulfonyl, carbamoyl, $C_{1-6}$ alkylcarbamoyl or aryl$C_{1-6}$ alkyl; and R 3 , together with the nitrogen atom to which it is attached, forms an optionally substituted 5 to 7 membered heterocyclic group fused to the benzene ring. Methods of preparing the compounds and uses of the compounds in therapy, in particular for a CNS disorder such as depression or anxiety, are also disclosed.

12 Claims, No Drawings

HETEROCYCLYMETHYLPIPERIDINES AND -PIPERAZINES POSSESSING AFFINITY AT 5HT-1 TYPE RECEPTORS

The present invention relates to novel compounds, processes for their preparation, pharmaceutical compositions containing the same and their use as medicaments in the treatment of CNS and other disorders.

A novel series of compounds has now been found that possess high affinity for 5-HT$_1$ type receptors and/or are 5-HT reuptake inhibitors. The present invention therefore provides, in a first aspect, a compound of formula (I) or a pharmaceutically acceptable salt thereof:

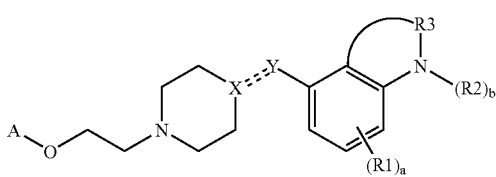

wherein:
A is optionally substituted phenyl, naphthyl, indolyl, quinolinyl, quinazolinyl, indazolyl, isoquinolinyl or benzofuranyl,
X is carbon, Y is CH and

:::::

is a double bond; or X is CH, Y is CH$_2$ or oxygen and

:::::

is a single bond; or X is nitrogen, Y is CH$_2$ and

:::::

is a single bond;
R1 is halogen, cyano, or C$_{1-6}$alkoxy;
a is 0, 1, 2 or 3;
b is 0 or 1;
R2 is hydrogen, C$_{1-6}$alkyl, C$_{1-6}$alkanoyl, fluoroC$_{1-6}$alkanoyl, C$_{1-6}$alkylsulfonyl, fluoroC$_{1-6}$alkylsulfonyl, carbamoyl, C$_{1-6}$alkylcarbamoyl or arylC$_{1-6}$alkyl; and
R3, together with the nitrogen atom to which it is attached, forms an optionally substituted 5 to 7 membered heterocyclic group fused to the benzene ring.

The term "halogen" and its abbreviation "halo" refer to fluorine, chlorine, bromine or iodine.

The term "C$_{1-6}$alkyl" refers to an alkyl group having from one to six carbon atoms, in all isomeric forms, such as methyl, ethyl, propyl, isopropyl, butyl, isobutyl, sec-butyl, tert-butyl, pentyl, neopentyl, sec-pentyl, n-pentyl, isopentyl, tert-pentyl and hexyl.

The term "C$_{1-6}$alkoxy" refers to a straight chain or branched chain alkoxy (or "alkyloxy") group having from one to six carbon atoms, such as methoxy, ethoxy, propoxy, isopropoxy, butoxy, isobutoxy, sec-butoxy, tert-butoxy, pentoxy, neopentoxy, sec-pentoxy, n-pentoxy, isopentoxy, tertpentoxy and hexoxy.

The term "C$_{1-6}$alkanoyl" refers to an alkanoyl group having from 1 to 6 carbon atoms, such as methanoyl (or "formyl"), ethanoyl (or "acetyl"), propanoyl, isopropanoyl, butanoyl, isobutanoyl, sec-butanoyl, pentanoyl, neopentanoyl, sec-pentanoyl, isopentanoyl, tertpentanoyl and hexanoyl.

The term "fluoroC$_{1-6}$alkanoyl" refers to a fluorine-substituted C$_{1-6}$alkanoyl group such as CF$_3$CO. The term "fluoroC$_{1-6}$alkylsulfonyl" refers to a fluorine-substituted C$_{1-6}$alkylsulfonyl group such as CF$_3$SO$_2$—.

The term "carbamoyl" refers to the group H$_2$NCO. The term "C$_{1-6}$alkylcarbamoyl" refers to a group having the formula (C$_{1-6}$alkyl)HNCO, such as CH$_3$NHCO.

The term "aryl", whether alone or as part of another group, is intended, unless otherwise stated, to denote an aromatic carbocyclic or heterocyclic group such as phenyl, naphthyl, pyridyl or pyrazinyl, optionally substituted by one or more halogen, C$_{1-6}$alkyl, CF$_3$, cyano, hydroxy, C$_{1-6}$alkanoyl, or C$_{1-6}$alkoxy. Where used herein the term naphthyl, whether alone or as part of another group, is intended, unless otherwise stated, to denote both 1-naphthyl and 2-naphthyl groups.

The term "oxo" refers to the group "=O".

The term "optionally substituted 5 to 7 membered heterocyclic group" refers to an optionally substituted saturated or non-saturated ring containing at least one nitrogen atom and optionally a further 1 or 2 heteroatoms selected from nitrogen, sulphur or oxygen, the ring consisting of a total of 5 to 7 atoms. Examples of 5 to 7 membered heterocyclic groups include pyrrolidinyl, imidazolidinyl, pyrazolidinyl, oxazolidinyl, isothiazolidinyl, thiazolidinyl, pyrrolyl, pyrrolinyl, pyrazolinyl, imidazolyl, pyrazolyl, isothiazolyl, thiazolyl, piperidyl, piperazinyl, morpholinyl, thiomorpholinyl, pyridyl, pyridazinyl, pyrimidinyl, pyrazinyl, azepinyl and azepanyl. The heterocyclic group may be substituted by one or more, preferably 1 to 3, substituents, which may be the same or different, and which is selected from the following group: oxo, C$_{1-6}$alkyl, cyano, CF$_3$, C$_{1-6}$alkoxy and C$_{1-6}$alkanoyl.

The term "C$_{3-7}$cycloalkylC$_{1-6}$alkoxy" refers to a cycloalkyl group consisting of from 3 to 7 carbon atoms (for example cyclopropane, cyclobutane, cyclopentane, cyclohexane and cycloheptane) attached to an arylC$_{1-6}$alkoxy group.

When b is two or more, the two or more R2 groups may be the same or different.

A is optionally substituted phenyl, naphthyl, indolyl, quinolinyl, quinazolinyl, indazolyl, isoquinolinyl or benzofuranyl. These groups may be attached to the oxygen atom in formula (I) at any suitable position. These groups may be substituted by 1 to 4 substituents, which may be the same or different, and which are selected from the following group: halogen, hydroxy, cyano, CF$_3$, C$_{1-6}$alkyl, C$_{1-6}$alkoxy, C$_{1-6}$alkoxyC$_{1-6}$alkyl, C$_{3-7}$cycloalkylC$_{1-6}$alkoxy, C$_{1-6}$alkanoyl, C$_{1-6}$alkylsulfonyl, C$_{1-6}$alkylsulfinyl, C$_{1-6}$alkylsulfonyloxy, C$_{1-6}$alkylsulfonylC$_{1-6}$alkyl, C$_{1-6}$alkylsulfonamido, C$_{1-6}$alkylamido, C$_{1-6}$alkylsulfonamidoC$_{1-6}$alkyl and C$_{1-6}$alkylamidoC$_{1-6}$alkyl. Preferred optional substituents for A are C$_{1-6}$alkyl, cyano, CF$_3$, C$_{1-6}$alkoxy and C$_{1-6}$alkanoyl.

Preferably A is quinolinyl or quinazolinyl. Most preferably, A is 5-(2-methyl)quinolinyl or 5-(2-methyl)quinazolinyl.

Preferably Y is CH$_2$ or CH.

Preferably R1 is fluoro.

Preferably a is 0, 1 or 2.

When b is 1, preferably R2 is hydrogen, C1-6alkyl (particularly methyl, ethyl or propyl) or C1-6alkylsulfonyl.

R3, together with the nitrogen atom to which it is attached, forms an optionally substituted 5 to 7 membered heterocyclic group fused to the benzene ring. As clear from formula (I), the heterocyclic ring is fused to the benzene ring at the position which is ortho to both Y and to the nitrogen atom. Preferably, the optionally substituted 5 to 7 membered heterocyclic group, together with the phenyl ring to which it is attached, forms an optionally substituted benzoxazinone, benzoimidazolyl, quinoxalinyl or quinolinyl group.

Preferred compounds of this invention are:

8-{1-[2-(2-Methylquinolin-5-yloxy)ethyl]piperidin-4-yloxy}-4H-benzo[1,4]oxazin-3-one hydrochloride (E1)

5-{2-[4-(3H-Benzimidazol-4-ylmethyl)piperazin-1-yl]ethoxy}-2-methylquinoline (E2)

5-{4-[2-(2-Methylquinolin-5-yloxy)ethyl]piperazin-1-ylmethyl}quinoline (E3)

5-{4-[2-(2-Methylquinolin-5-yloxy)ethyl]piperazin-1-ylmethyl}quinoxaline (E4)

8-{1-[2-(2-Methylquinolin-5-yloxy)ethyl]piperidin-4-ylmethyl}4H-benzo[1,4]oxazin-3-one (E5)

8-{1-[2-(7-Fluoro-2-methylquinolin-5-yloxy)ethyl]piperidin-4-ylmethyl}-4H-benzo[1,4]oxazin-3-one (E6)

8-{1-[2-(7-Chloro-2-methylquinolin-5-yloxy)ethyl]piperidin-4-ylmethyl}-4H-benzo[1,4]oxazin-3-one (E7)

8-{1-[2-(2-Methylquinazolin-5-yloxy)ethyl]piperidin-4-ylmethyl}-4H-benzo[1,4]oxazin-3-one (E8)

4-Methyl-8-{1-[2-(2-methylquinolin-5-yloxy)ethyl]piperidin-4-ylmethyl}-4H-benzo[1,4]oxazin-3-one (E9)

8-{1-[2-(7-Fluoro-2-methylquinolin-5-yloxy)ethyl]piperidin-4-ylmethyl}-4-methyl-4H-benzo[1,4]oxazin-3-one (E10)

8-{1-[2-(7-Chloro-2-methylquinolin-5-yloxy)ethyl]piperidin-4-ylmethyl}-4-methyl-4H-benzo[1,4]oxazin-3-one (E11)

4-Methyl-8-{1-[2-(2-methylquinazolin-5-yloxy)ethyl]piperidin-4-ylmethyl}-4H-benzo[1,4]oxazin-3-one (E12)

and pharmaceutically acceptable salts thereof.

The compounds of formula (I) can form acid addition salts thereof. It will be appreciated that for use in medicine the salts of the compounds of formula (I) should be pharmaceutically acceptable. Suitable pharmaceutically acceptable salts will be apparent to those skilled in the art and include those described in J. Pharm. Sci., 1977, 66, 1–19, such as acid addition salts formed with inorganic acids e.g. hydrochloric, hydrobromic, sulfuric, nitric or phosphoric acid; and organic acids e.g. succinic, maleic, acetic, fumaric, citric, tartaric, benzoic, p-toluenesulfonic, methanesulfonic or naphthalenesulfonic acid. Certain of the compounds of formula (I) may form acid addition salts with one or more equivalents of the acid. The present invention includes within its scope all possible stoichiometric and non-stoichiometric forms.

The compounds of formula (I) may be prepared in crystalline or non-crystalline form, and, if crystalline, may optionally be hydrated or solvated. This invention includes within its scope stoichiometric hydrates or solvates as well as compounds containing variable amounts of water and/or solvent.

Certain compounds of formula (I) are capable of existing in stereoisomeric forms (e.g. geometric or ("cis-trans") isomers, diastereomers and enantiomers) and the invention extends to each of these stereoisomeric forms and to mixtures thereof including racemates. The different stereoisomeric forms may be separated one from the other by the usual methods, or any given isomer may be obtained by stereospecific or asymmetric synthesis. The invention also extends to any tautomeric forms and mixtures thereof. The present invention includes within its scope all such isomers, including mixtures.

In a further aspect, this invention provides a process for the preparation of a compound of formula (I) or a pharmaceutically acceptable salt thereof, which process comprises:

(a) the coupling of a compound of formula (II):

wherein A is as defined for formula (I) and L is a leaving group, with a compound of formula (III):

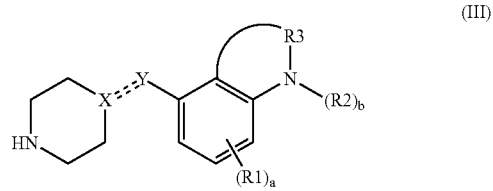

wherein a, b, R1, R2, R3, X, Y and

are as defined for formula (I);

or (b) for a compound wherein X is nitrogen, the coupling of a compound of formula (IV):

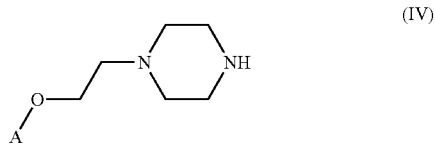

wherein A is as defined for formula (I), with a compound of formula (V):

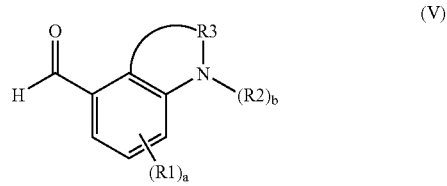

wherein a, b, R1, R2 and R3 are as defined for formula (I); and thereafter optionally for process (a) or process (b):

removing any protecting groups and/or converting a compound of formula (I) into another compound of formula (I) and/or forming a pharmaceutically acceptable salt.

For process (a), the reaction of compounds of formulae (II) and (III) is preferably carried out in a suitable solvent such as isopropyl alcohol or N,N-dimethylformamide, in the presence of an appropriate base such as N,N-diisopropylethylamine or potassium carbonate. A suitable leaving group L is bromine.

For process (b), the reaction of compounds of formulae (IV) and (V) is preferably carried out in an aprotic solvent such as 1,2-dichloroethane, in the presence of an appropriate reducing agent such as sodium triacetoxyborohydride.

Compounds of formula (I) can be converted into further compounds of formula (I) using standard techniques. For example, and by way of illustration rather than limitation, for compounds of formula (I) wherein

===== is a double bond can be converted to compounds of formula (I) in which

===== is a single bond by palladium catalysed hydrogenation in a suitable solvent such as ethanol. Other possible conversion reactions include acylation with an appropriate acylating agent such as acetyl chloride, alkylation using an appropriate alkylating reagent such as methyl iodide, and sulfonylation using a sulfonylating agent such as methanesulfonic anhydride.

Compounds of formulae (II), (III), (IV) and (V) are commercially available, may be prepared according to procedures described herein, by known literature methods, or by analogous procedures thereto.

For example, for compounds of the present invention wherein X is carbon, Y is CH and

===== is a double bond, compounds of formula (III) wherein X is carbon may be prepared by reacting a compound of formula (VI):

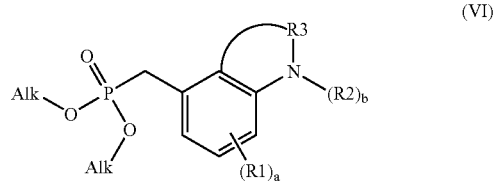

(VI)

wherein "Alk" refers to an alkyl group, with a compound of formula (VII):

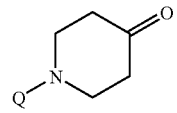

(VII)

wherein Q is a protecting group such as t-butyloxycarbonyl, in the presence of a base such as sodium hydride, in a solvent such as tetrahydrofuran or N,N-dimethylformamide. The protecting group Q may be removed thereafter by any suitable means.

Compounds of formula (VI) may be prepared by treating a compound of formula (VIII):

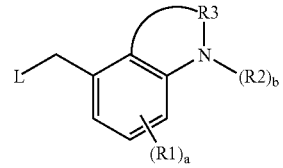

(VIII)

wherein L is a leaving group such as bromine, with a trialkyl phosphite such as triethyl phosphite or trimethyl phosphite, in the absence of solvent or in the presence of a solvent such as toluene.

It will be appreciated by those skilled in the art that it may be necessary to protect certain reactive substituents during some of the above procedures. Standard protection and deprotection techniques, such as those described in Greene T. W. *Protective groups in organic synthesis*, New York, Wiley (1981), can be used. For example, primary amines can be protected as phthalimide, benzyl, t-butyloxycarbonyl, benzyloxycarbonyl or trityl derivatives. Carboxylic acid groups can be protected as esters. Aldehyde or ketone groups can be protected as acetals, ketals, thioacetals or thioketals. Deprotection of such groups is achieved using conventional procedures well known in the art. For example, protecting groups such as t-butyloxycarbonyl may be removed using an acid such as hydrochloric or trifluroroacetic acid in a suitable solvent such as dichloromethane, diethylether, isopropanol or mixtures thereof.

Pharmaceutically acceptable salts may be prepared conventionally by reaction with the appropriate acid or acid derivative.

The affinities of the compounds of this invention for $5\text{-HT}_{1A}$, $5\text{-HT}_{1B}$ and $5\text{-HT}_{1D}$ receptors can be determined by the radioligand binding assay as described in WO 99/07700. All compounds tested according to the radioligand binding assay described above were found to have pKi values >6.0 at $5\text{-HT}_{1A}$, $5\text{-HT}_{1B}$ and $5\text{-HT}_{1D}$ receptors, with many showing a considerably higher affinity (having pKi values in the range 8.0–10.0).

The intrinsic activity of the compounds of this invention can be determined according to the [$^{35}$S]GTPγS functional assay which is also described in WO 99/07700. It has been found, using the [$^{35}$S]GTPγS functional assay, that certain compounds of formula (I) appear to be antagonists at $5\text{-HT}_1$ type receptors whilst others appear to be inverse agonists, agonists or partial agonists.

The efficacy of the compounds of this invention to inhibit the re-uptake of serotonin can be measured in a 5-HT uptake assay by measurement of uptake of [$^3$H]-5-HT into rat cortical synaptosomes as described in Thomas, D. R.; Nelson, D. R.; and Johnson, A. M. *Psychopharmacology* 93:193–200 (1987). Some of the compounds of the present invention were tested according to this 5-HT uptake assay and were found to have potency at the uptake site of pKi>6.0. Some compounds tested had a pKi value of >8.0.

Concomitant blockade of 5-HT$_{1A}$, 5-HT$_{1B}$ and 5-HT$_{1D}$ autoreceptors or alternatively blockade of 5-HT$_{1A}$, 5-HT$_{1B}$ and 5-HT$_{1D}$ autoreceptors, in addition to the blockade of serotonin reuptake transporter, has been found to elevate synaptic 5-HT and increase serotonergic transmission, and acutely mimic the effects of chronic treatment with SSRIs. This is expected to result in advantages of increased efficacy, faster onset and a favourable side-effect profile in the clinic.

Compounds of formula (I) and their pharmaceutically acceptable salts are of use in the treatment of certain CNS disorders such as depression (both bipolar and unipolar), single or recurrent major depressive episodes with or without psychotic features, catatonic features, melancholic features, atypical features or postpartum onset, seasonal affective disorder and dysthymia, anxiety disorders, including generalised anxiety, schizophrenia, panic disorder, agoraphobia, social phobia, obsessive compulsive disorder and post-traumatic stress disorder; pain (particularly neuropathic pain); memory disorders, including dementia, amnesic disorders and age-associated memory impairment; disorders of eating behaviours, including anorexia nervosa and bulimia nervosa, sexual dysfunction, sleep disorders (including disturbances of circadian rhythm, dyssomnia, insomnia, sleep apnea and narcolepsy), withdrawal from abuse of drugs such as of cocaine, ethanol, nicotine, benzodiazepines, alcohol, caffeine, phencyclidine (phencyclidine-like compounds), opiates (e.g. cannabis, heroin, morphine), sedative ipnotic, amphetamine or amphetamine-related drugs (e.g. dextroamphetamine, methylamphetamine) or a combination thereof, motor disorders such as Parkinson's disease, dementia in Parkinson's disease, neuroleptic-induced Parkinsonism and tardive dyskinesias, as well as other psychiatric disorders. Depressive disorders which may be treated or prevented by the compounds of formula (I) and their pharmaceutically acceptable salts may also result from a general medical condition including, but not limited to, myocardial infarction, diabetes, miscarriage or abortion, etc. Compounds of formula (I) may also have utility in the treatment of certain gastrointestinal disorders such as irritable bowel syndrome.

It is to be understood that "treatment" as used herein includes prophylaxis as well as alleviation of established symptoms.

Thus the invention also provides a compound of formula (I) or a pharmaceutically acceptable salt thereof, for use as a therapeutic substance, in particular in the treatment of the above disorders. In particular the invention provides a compound of formula (I) or a pharmaceutically acceptable salt thereof for use as a therapeutic substance in the treatment of a CNS disorder, particularly depression or anxiety.

Compounds of the invention may be administered in combination with other active substances such as 5HT3 antagonists, serotonin agonists, NK-1 antagonists, selective serotonin reuptake inhibitors (SSRI), noradrenaline re-uptake inhibitors (SNRI), tricyclic antidepressants and/or dopaminergic antidepressants.

Suitable 5HT3 antagonists which may be used in combination of the compounds of the inventions include for example ondansetron, granisetron, metoclopramide.

Suitable serotonin agonists which may be used in combination with the compounds of the invention include sumatriptan, rauwolscine, yohimbine, metoclopramide.

Suitable SSRIs which may be used in combination with the compounds of the invention include fluoxetine, citalopram, femoxetine, fluvoxamine, paroxetine, indalpine, sertraline, zimeldine.

Suitable SNRIs which may be used in combination with the compounds of the invention include venlafaxine and reboxetine.

Suitable tricyclic antidepressants which may be used in combination with a compound of the invention include imipramine, amitriptiline, chlomipramine and nortriptiline.

Suitable dopaminergic antidepressants which may be used in combination with a compound of the invention include bupropion and amineptine.

It will be appreciated that the compounds of the combination or composition may be administered simultaneously (either in the same or different pharmaceutical formulations), separately or sequentially.

The invention further provides a method of treatment of the above disorders, particularly a CNS disorder such as depression or anxiety, in mammals including humans, which comprises administering to the sufferer a therapeutically safe and effective amount of a compound of formula (I) or a pharmaceutically acceptable salt thereof.

In another aspect, the invention provides for the use of a compound of formula (I) or a pharmaceutically acceptable salt thereof in the manufacture of a medicament for use in the treatment of the above disorders, particularly a CNS disorder such as depression or anxiety.

In order to use the compounds of formula (I) in therapy, they will normally be formulated into a pharmaceutical composition in accordance with standard pharmaceutical practice. The present invention also provides a pharmaceutical composition, which comprises a compound of formula (I) or a pharmaceutically acceptable salt thereof, and a pharmaceutically acceptable carrier or excipient.

In a further aspect, the present invention provides a process for preparing a pharmaceutical composition, the process comprising mixing a compound of formula (I) or a pharmaceutically acceptable salt thereof and a pharmaceutically acceptable carrier or excipient.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrable compositions are generally preferred.

Tablets and capsules for oral administration may be in unit dose form, and may contain conventional excipients, such as binding agents (e.g. pregelatinised maize starch, polyvinylpyrrolidone or hydroxypropyl methylcellulose); fillers (e.g. lactose, microcrystalline cellulose or calcium hydrogen phosphate); tabletting lubricants lubricants (e.g. magnesium stearate, talc or silica); disintegrants (e.g. potato starch or sodium starch glycollate); and acceptable wetting agents (e.g. sodium lauryl sulphate). The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents (e.g. sorbitol syrup, cellulose derivatives or hydrogenated edible fats), emulsifying agents (e.g. lecithin or acacia), non-aqueous vehicles (which may include edible oils e.g. almond oil, oily esters, ethyl alcohol or fractionated vegetable oils), preservatives (e.g. methyl or propyl-p-hydroxybenzoates or sorbic acid), and, if desired, conventional flavourings or colorants, buffer salts and sweetening agents as appropriate. Preparations for oral administration may be suitably formulated to give controlled release of the active compound.

For parenteral administration, fluid unit dosage forms are prepared utilising a compound of the invention or pharmaceutically acceptable salt thereof and a sterile vehicle. Formulations for injection may be presented in unit dosage form e.g. in ampoules or in multi-dose, utilising a compound of the invention or pharmaceutically acceptable salt thereof and a sterile vehicle, optionally with an added preservative. The compositions may take such forms as suspensions, solutions or emulsions in oily or aqueous vehicles, and may contain formulatory agents such as suspending, stabilising and/or dispersing agents.

Alternatively, the active ingredient may be in powder form for constitution with a suitable vehicle, e.g. sterile pyrogen-free water, before use. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

Lotions may be formulated with an aqueous or oily base and will in general also contain one or more emulsifying agents, stabilising agents, dispersing agents, suspending agents, thickening agents, or colouring agents. Drops may be formulated with an aqueous or non-aqueous base also comprising one or more dispersing agents, stabilising agents, solubilising agents or suspending agents. They may also contain a preservative.

The compounds of the invention may also be formulated in rectal compositions such as suppositories or retention enemas, e.g. containing conventional suppository bases such as cocoa butter or other glycerides.

The compounds of the invention may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

For intranasal administration, the compounds of the invention may be formulated as solutions for administration via a suitable metered or unitary dose device or alternatively as a powder mix with a suitable carrier for administration using a suitable delivery device. Thus compounds of formula (I) may be formulated for oral, buccal, parenteral, topical (including ophthalmic and nasal), depot or rectal administration or in a form suitable for administration by inhalation or insufflation (either through the mouth or nose).

The compounds of the invention may be formulated for topical administration in the form of ointments, creams, gels, lotions, pessaries, aerosols or drops (e.g. eye, ear or nose drops). Ointments and creams may, for example, be formulated with an aqueous or oily base with the addition of suitable thickening and/or gelling agents. Ointments for administration to the eye may be manufactured in a sterile manner using sterilised components.

The composition may contain from 0.1% to 99% by weight, preferably from 10 to 60% by weight, of the active material, depending on the method of administration. The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 1.0 to 200 mg, and such unit doses may be administered more than once a day, for example two or three times a day. Such therapy may extend for a number of weeks or months.

All publications, including but not limited to patents and patent applications, cited in this specification are herein incorporated by reference as if each individual publication were specifically and individually indicated to be incorporated by reference herein as though fully set forth.

The following Descriptions and Examples illustrate the preparation of compounds of the invention.

Description 1 tert-Butyl 4-[2-(2-methylquinolin-5-yloxy)ethyl]piperazine-1-carboxylate (D1)

tert-Butyl piperazine-1-carboxylate (1.4 g, 7.52 mmol) was added to a mixture of 5-(2-bromoethoxy)-2-methylquinoline (2 g, 7.52 mmol) and potassium carbonate (4.16 g, 30.1 mmol) in N,N-dimethylformamide (20 mL). The reactants were heated at 70° C. for 16 h under an atmosphere of argon. The reaction mixture was poured into water (200 mL) and extracted into ethyl acetate (3×200 mL). The organic layers were combined, dried ($Na_2SO_4$) and concentrated in vacuo. The residue was purified by column chromatography, eluting with 30% ethyl acetate in hexane affording the title compound as a tan solid (1.04 g, 37%).

Mass spectrum (API$^+$): Found 372.3 (MH$^+$). $C_{21}H_{29}N_3O_3$ requires 371. $^1$H NMR (CDCl$_3$) δ: 1.46 (9H, s), 2.59 (4H, t), 2.73 (3H, s), 2.96 (2H, t), 3.46 (4H, t), 4.29 (2H, t), 6.80 (1H, dd), 7.26 (1H, d), 7.58 (2H, m), 8.43 (1H, d).

Description 2

2-Methyl-5-(2-piperazin-1-ylethoxy)quinoline (D2)

tert-Butyl 4-[2-(2-methylquinolin-5-yloxy)ethyl]piperazine-1-carboxylate (1.04 g, 2.8 mmol) was dissolved in ethanol (60 mL) and treated with 1M hydrochloric acid in diethyl ether (16 mL, 16 mmol) and stirred at 40° C. for 17 h. The reaction mixture was filtered and the white solid was collected and dried in vacuo. The hydrochloride salt precipitate was dissolved in water (25 mL) and potassium carbonate was added until the pH reached 10. The aqueous layer was washed with 5% methanol in dichloromethane (4×100 mL) then 10% methanol in dichloromethane (4×100 mL). The organic layers were combined, dried ($Na_2SO_4$) and concentrated in vacuo, affording the title compound as a brown oil (0.69 g, 91%).

Mass spectrum (API+): Found 272 (MH+). $C_{16}H_{21}N_3O$ requires 271.

$^1$H NMR (CDCl$_3$, free base) δ: 2.62 (4H, m), 2.73 (3H, s), 2.92 (6H, m), 3.47 (1H, s), 4.29 (2H, d), 6.80 (1H, dd), 7.50 (1H, d), 7.58 (2H, m), 8.45 (1H, d).

Description 3

5-Bromo-2-methoxy-3-nitrobenzaldehyde (D3)

5-Bromo-2-methoxybenzaldehyde (29.65 g, 138 mmol) was added to stirred concentrated sulfuric acid (160 mL) at −15° C. Nitric acid (70% w/w) (16 g) was added dropwise. Further stirring was allowed for 15 mins at this temperature before the mixture was poured onto crushed ice (2 L). The resulting precipitate was collected by filtration and partitioned between dichloromethane (800 mL) and saturated sodium hydrogen carbonate (1 L). The organic layer was dried (Na$_2$SO$_4$) and evaporated in vacuo to give the title compound (20.5 g) as a crude solid.

$^1$H NMR (CDCl$_3$) δ: 4.08 (3H, s), 8.17–8.22 (2H, m), 10.32 (1H, s).

Description 4

5-Bromo-2-methoxy-3-nitrobenzyl Alcohol (D4)

Sodium borohydride (4 g) was added in portions to a stirring solution of crude 5-bromo-2-methoxy-3-nitrobenzaldehyde (20.5 g) in methanol (350 mL) and tetrahydrofuran (150 mL) at 0° C. After 1 h, the methanol was removed in vacuo. The residue was treated with cold water (150 mL) and extracted with diethyl ether (2×150 mL). The combined organic layer was evaporated in vacuo to give a crude oil. Silica gel chromatography eluting with ethyl acetate in petroleum ether (10–40%) gave the title compound (17 g) as a solid.

$^1$H NMR (CDCl$_3$) δ: 2.00 (1H, t, J=6 Hz), 3.92 (3H, s), 4.80 (2H, d, J=6 Hz), 7.84 (1H, d, J=2 Hz), 7.91 (1H, d, J=2 Hz).

Description 5

5-Bromo-2-methoxy-3-nitrobenzyl Bromide (D5)

2,6-Lutidine (10.5 mL) was added to a stirring solution of 5-bromo-2-methoxy-3-nitrobenzyl alcohol (13.6 g) and lithium bromide (11.75 g) in anhydrous tetrahydrofuran (200 mL) at 0° C. A solution of methanesulfonic anhydride (11.8 g) in anhydrous tetrahydrofuran (20 mL) was added dropwise. The resulting mixture was left to stir at room temperature for 16 h. It was partitioned between diethyl ether (250 mL) and saturated sodium hydrogen carbonate (150 mL). The organic layer was dried (sodium sulfate) and evaporated in vacuo. Silica gel chromatography of the crude residue eluting with diethyl ether in petroleum ether gave the title compound (20 g) as an amber oil.

$^1$H NMR (CDCl$_3$) δ: 4.06 (3H, s), 4.48 (2H, s), 7.76 (1H, d, J=2 Hz), 7.93 (1H, d, J=2 Hz).

Description 6 tert-Butyl 4-(5-bromo-2-methoxy-3-nitrobenzylidene)piperidine-1-carboxylate (D6)

A mixture of 5-bromo-2-methoxy-3-nitrobenzyl bromide (8.4 9, 26 mmol) and triethyl phosphite (4.5 g, 27 mmol) was heated to 160° C. for 2 h and then evaporated in vacuo to give a dark amber oil. This was dissolved in anhydrous tetrahydrofuran (20 mL) and added dropwise to a stirring suspension of sodium hydride (60%) (1.14 g) in anhydrous N,N-dimethylformamide (100 mL) at 0° C. The mixture was left to stir for 1 hour. tert-Butyl 4-oxopiperidine-1-carboxylate (5.17 g, 26 mmol) in anhydrous THF (30 mL) was added to the mixture. Stirring was continued for 4 h at room temperature before the mixture was poured into saturated ammonium chloride (100 mL) and extracted with diethyl ether (2×150 mL). The combined organic layer was evaporated in vacuo to give a crude oil. Silica gel chromatography eluting with diethyl ether in petroleum ether (5–30%) gave the title compound (3.9 g, 35%) as an oil.

$^1$H NMR (CDCl$_3$) δ: 1.48 (9H, s), 2.25–2.45 (4H, m), 3.35–3.58 (4H, m), 3.84 (3H, s), 6.29 (1H, s), 7.46 (1H, d, J=2 Hz), 7.79 (1H, d, J=2 Hz).

Description 7 tert-Butyl 4-(5-bromo-2-hydroxy-3-nitrobenzylidene)piperidine-1-carboxylate (D7)

A mixture of tert-butyl 4-(5-bromo-2-methoxy-3-nitrobenzylidene)piperidine-1-carboxylate (2.5 g, 5.9 mmol) and lithium chloride (1 g) in anhydrous N,N-dimethylformamide was stirred at 120° C. for 4 h. It was allowed to cool to room temperature and evaporated in vacuo. The residue was treated with water (50 mL) and extracted with diethyl ether (2×100 mL). The combined organic layers was washed with water (50 mL) and dried (Na$_2$SO$_4$). Evaporation of solvent gave the title compound as a crude oil (2.1 g).

$^1$H NMR (CDCl$_3$) δ: 1.48 (9H, s), 2.20–2.40 (4H, m), 3.34–3.55 (4H, m), 6.25 (1H, s), 7.43 (1H, s), 7.76 (1H, s).

Description 8 tert-Butyl 4-(3-oxo-3,4-dihydro-2H-benzo[1,4]oxazin-8-ylmethyl)piperidine-1-carboxylate (D8)

A solution of tert-butyl 4-(5-bromo-2-hydroxy-3-nitrobenzylidene)piperidine-1-carboxylate (2.1 g, 4.9 mmol) in methanol (150 mL) was stirred under atmospheric hydrogen in the presence of 10% palladium on charcoal (0.5 g) for 4 h. The catalyst was removed by filtration and the filtrate was evaporated in vacuo to give a crude oil (1.8 g) which was taken up in 2-butanone (30 mL) and aqueous sodium hydrogen carbonate (1.3 g in water 20 mL). Chloroacetyl chloride (0.78 g) was added dropwise at 0° C. The mixture was stirred at 0° C. for further 2 h and then at 80° C. for 4 h. It was partitioned between water (50 mL) and ethyl acetate (100 mL). The organic layer was evaporated in vacuo. Silica gel chromatography of the resulting residue eluting with ethyl acetate in petroleum ether (20–30%) gave the title compound (1.5 g) as an oil.

$^1$H NMR (CDCl$_3$) δ: 1.10–1.20 (2H, m), 1.45 (9H, s), 1.55–1.64 (2H, m), 1.64–1.74 (1H, m), 2.56 (2H, d, J=8 Hz), 2.57–2.76 (2H, m), 4.00–4.15 (2H, m), 4.60 (2H, s), 6.64 (1H, d, J=8 Hz), 6.80 (1H, d, J=8Hz), 6.88 (1H, t, J=8 Hz), 7.60 (1H, s).

Description 9 tert-Butyl 4-(4-methyl-3-oxo-3,4-dihydro-2H-benzo[1,4]oxazin-8-ylmethyl)piperidine-1-carboxylate (D9)

A solution of tert-butyl 4-(3-oxo-3,4-dihydro-2H-benzo[1,4]oxazin-8-ylmethyl)piperidine-1-carboxylate (0.6 g, 1.73 mmol) in anhydrous N,N-dimethylformamide (1 mL), was added dropwise to a stirred suspension of sodium hydride (60%) (0.08 g) in anhydrous N,N-dimethylformamide (12 mL) at 0° C. Stirring was continued for a further 20 mins. before iodomethane (0.5 g) in anhydrous N,N-dimethylformamide (1 mL) was added. The mixture was allowed to stir at room temperature for 4 hours. It was quenched with saturated ammonium chloride (20 mL) and extracted with diethyl ether (100 mL). The organic layer was dried (Na$_2$SO$_4$) and evaporated in vacuo to give a crude oil. Silica gel chromatography eluting with ethyl acetate in hexane (10–20%) gave the title compound as a solid (0.6 g, 97%).

¹H NMR (CDCl₃) δ: 1.10–1.20 (2H, m), 1.45 (9H, s), 1.53–1.75 (3H, m), 2.57 (2H, d, J=8 Hz), 2.58–2.70 (2H, m), 3.36 (3H, s), 3.96–4.15 (2H, m), 4.58 (2H, s), 6.84 (2H, m), 6.96 (1H, t, J=8 Hz).

Description 10

8-(Piperidin-4-ylmethyl)-4H-benzo[1,4]oxazin-3-one (D10)

The title compound was prepared from tert-butyl 4-(3-oxo-3,4-dihydro-2H-benzo[1,4]oxazin-8-ylmethyl)piperidine-1-carboxylate following the method of Description 2.

Description 11

4-Methyl-8-(piperidin-4-ylmethyl)-4H-benzo[1,4]oxazin-3-one (D11)

The title compound was prepared from tert-butyl 4-(4-methyl-3-oxo-3,4-dihydro-2H-benzo[1,4]oxazin-8-ylmethyl)piperidine-1-carboxylate following the method of Description 2.

Description 12

5-Fluoro-2-methyl-3,4-dihydroquinazoline (D12)

A solution of 2-amino-6-fluorobenzylamine (1.1 g, 7.86 mmol) and triethylorthoacetate (1.58 mL, 8.64 mmol) in ethanol (30 mL) was heated at 80° C. for 14 h. The reaction mixture was allowed to cool to room temperature and evaporated in vacuo. The yellow oil was triturated with diethyl ether to give the title compound as white solid (0.74 g, 57%).

Mass spectrum (API⁺): Found 165 (MH⁺). C₉H₉N₂F requires 164.

¹H NMR (CDCl₃) δ: 2.02 (3H, s), 4.67 (2H, s), 6.34–6.71 (2H, m), 7.03–7.12 (1H, m).

Description 13

5-Fluoro-2-methylquinazoline (D13)

To a solution of 5-fluoro-2-methyl-3,4-dihydroquinazoline (0.74 g, 4.51 mmol) in chloroform (100 mL) at room temperature was added manganese (IV) oxide (4.0 g, 46.0 mmol) and the reaction mixture stirred at room temperature for 20 h. The reaction mixture was filtered through a plug of celite, washing with dichloromethane. The filtrate was evaporated in vacuo to give the title compound as a yellow solid (0.715 g, 98%).

Mass spectrum (API⁺): Found 163 (MH⁺). C₉H₇N₂F requires 162.

¹H NMR (CDCl₃) δ: 2.92 (3H, s), 7.19–7.27 (1H, m), 7.77–7.83 (2H, m), 9.60 (1H, s).

Description 14

2-(2-Methylquinazolin-5-yloxy)ethanol (D14)

To a solution of ethylene glycol (3.05 mL, 55.6 mmol) in N,N-dimethylformamide (50 mL) at room temperature was added sodium hydride (60% dispersion in oil, 0.30 g, 7.50 mmol) portion-wise. The reaction mixture was allowed to stir at room temperature for 30 minutes. A solution of 5-fluoro-2-methylquinazoline (2.22 g, 55.6 mmol) in N,N-dimethylformamide (5 mL) was added and the reaction mixture heated at 85° C. for 14 h. The mixture was allowed to cool to room temperature, quenched by the addition of water and concentrated in vacuo. Chromatography of the residue on SiO₂ eluting with 40% ethyl acetate in dichloromethane to ethyl acetate gave the title compound as a yellow solid (0.39 g, 10%).

Mass spectrum (API⁺): Found 205 (MH⁺) C₁₁H₁₂N₂O₂ requires 204.

¹H NMR (CDCl₃) δ: 2.87 (3H, s), 4.13–4.16 (2H, m), 4.31–4.33 (2H, m), 6.88 (1H, d, J=8 Hz), 7.50 (1H, d, J=9 Hz), 7.72–7.76 (1H, m), 9.64 (1H, s).

Description 15

5-(2-(Methanesulphonyloxy)ethoxy)-2-methylquinazoline (D15)

To a solution of 2-(2-methylquinazolin-5-yloxy)ethanol (0.330 g, 1.62 mmol) in dichloromethane (20 mL) and triethylamine (0.34 mL, 2.43 mmol) was added methane sulfonyl chloride (0.14 mL, 1.78 mmol) dropwise. The reaction mixture was allowed to stir at room temperature for 2 h. The reaction mixture was diluted with further dichloromethane and partitioned with saturated NaHCO₃ aq. The organic phase was washed with brine, dried (MgSO₄) and evaporated in vacuo to give the title compound as a cream solid (0.452 g, 99%).

Mass spectrum (ES⁺): Found 283 (MH⁺) C₁₂H₁₄N₂O₄S requires 282.

¹H NMR (CDCl₃) δ: 2.89 (3H, s), 3.10 (3H, s), 4.46–4.48 (2H, m), 4.71–4.73 (2H, m), 6.86 (1H, d, J=8 Hz), 7.74–7.78 (1H, d, J=9 Hz), 7.74–7.78 (1H, m), 9.69 (1H, s).

Description 16

2-(5-Quinolinyloxy)ethyl Bromide (D16)

A mixture of 5-hydroxyquinoline (0.3 g, 2.1 mmol), 1,2-dibromoethane (3.9 g, 21 mmol) and potassium carbonate (1.5 g, 11 mmol) in methyl ethyl ketone (15 mL) was allowed to stir at 85° C. for 24 h. The mixture was evaporated in vacuo and the residue was partitioned between ether (200 mL) and water (200 mL). The organic layer was dried (Na₂SO₄) and evaporated in vacuo to give the title compound (0.53 g).

¹H NMR (CDCl₃) δ: 3.80 (2H, m), 4.49 (2H, m), 6.86 (1H, d, J=8 Hz), 7.41 (1H, dd, J=8, 4 Hz), 7.61 (1H, t, J=8 Hz), 7.73 (1H, d, J=8 Hz), 8.64 (1H, d, J=8 Hz), 8.91 (1H, m).

Description 17

5-Hydroxy-2-methylquinoline (D17)

A mixture of 2-methyl-5,6,7,8-tetrahydroquinolin-5-one [E. Reimann, J. Freisinger, Arch. Pharm. (Weinheim), 318, 871 (1985)] (0.57 g, 3.5 mmol) and 48% aqueous HBr (3.5 mL) was warmed to 60° C. and treated dropwise with bromine (0.19 mL, 0.59 g, 3.6 mmol), with vigorous stirring. The resulting mixture was stirred at 60° C. for 1 h, then evaporated in vacuo. The residue was treated with isopropanol with stirring, then the mixture was evaporated in vacuo to give a waxy solid, which was triturated with 1:1 isopropanol-ether to give a beige powder (0.9 g). A mixture of this material, lithium carbonate (0.48 g, 6.7 mmol), lithium bromide (0.28 g, 3.2 mmol) and N,N-dimethylformamide (10 mL) was heated at 150° C. under argon with stirring for 2 h. The mixture was cooled then evaporated in vacuo. Chromatography of the residue on silica with 0–100% ethyl acetate-hexane gradient elution gave the title compound (0.28 g, 49%) as a solid.

Mass spectrum (API⁺): Found 160 (MH⁺). C₁₀H₉NO requires 159.

Description 18

5-(2-Bromoethoxy)-2-methylquinoline (D18)

The title compound was prepared from 5-hydroxy-2-methylquinoline and 1,2-dibromoethane using a similar procedure to Description 16, in 91% yield.

Mass spectrum (API$^+$): Found 266 (MH$^+$). C$_{12}$H$_{12}$$^{79}$BrNO requires 265.

Description 19

4-Hydroxy-3-nitrophenyl Benzoate (D19)

To a stirred solution of 4-hydroxyphenyl benzoate (10 g, 47 mmol) in acetic acid (250 mL) was added, dropwise with external ice-bath cooling, nitric acid (d=1.42, 2.9 mL) (T=10° C.). The mixture was warmed to 20° C. and stirred for a further 56 h. The solution was evaporated in vacuo and water added to the residue. The resulting yellow solid was collected by filtration, washed with water and dried in vacuo to give the title compound (11.8 g, 97%).

$^1$H NMR (CDCl$_3$) δ: 7.23 (1H, d), 7.53 (3H, m), 7.67 (1H, m), 8.00 (1H, d), 8.17 (2H, m), 10.52 (1H, s).

Description 20

4-(Methoxycarbonylmethoxy)-3-nitrophenyl Benzoate (D20)

A mixture of 4-hydroxy-3-nitrophenyl benzoate (48.8 g, 0.19 mol), methyl bromoacetate (28.8 g, 0.19 mol), anhydrous potassium carbonate (33.8 g, 0.24 mol) and acetone (700 mL) was heated at reflux for 24 h. The mixture was evaporated in vacuo and the residue partitioned between aqueous NaOH (1 M, 1 L) and dichloromethane (3×200 mL). The combined organic extracts were washed with aqueous NaOH (1 M, 500 mL), water (500 mL) and brine (250 mL), then dried (Na$_2$SO$_4$) and evaporated in vacuo to give a solid. Crystallisation from methanol following decolourisation with charcoal gave the title compound (38 g, 61%) as pale yellow needles.

$^1$H NMR (CDCl$_3$) δ: 3.83 (3H, s), 4.82 (2H, s), 7.08 (1H, d, J=9 Hz), 7.45 (1H, dd, J=9, 2 Hz), 7.56 (2H, m), 7.67 (1H, m), 7.83 (1H, d, J=2 Hz), 8.19 (2H, m).

Description 21

4-(Methoxycarbonylmethoxy)-3-nitrophenol (D21)

To a stirred suspension of 4-(methoxycarbonylmethoxy)-3-nitrophenyl benzoate (26.2 g, 79 mmol) in methanol (600 mL) at 20° C. was added, dropwise over 0.3 h, a solution of sodium methoxide (4.7 g, 87 mmol) in methanol (300 mL). The resulting mixture was stirred at 20° C. for 2 h then at 50° C. for 1 h. The solution was concentrated to 200 mL in vacuo, then poured into water (1 L) and extracted with ether-hexane (1:5, 500 mL). The aqueous phase was neutralised with 2M hydrochloric acid, then extracted with dichloromethane (6×300 mL). The combined dichloromethane extracts were dried (Na$_2$SO$_4$) and evaporated in vacuo to give a semi-solid, which was triturated with diethyl ether-hexane (1:3, 2×100 mL) to give the title compound (15.3 g, 85%) as a yellow solid.

$^1$H NMR (CDCl$_3$) δ: 2.00 (1H, br s), 3.80 (3H, s), 4.70 (2H, s), 6.95 (1H, d, J=9 Hz), 7.01 (1H, dd, J=9,2 Hz), 7.33 (1H, d, J=2 Hz).

Description 22

Methyl 4-(4-(N-(t-butyloxycarbonyl)piperidinyl)oxy)-2-nitrophenoxyacetate (D22)

To a stirred solution of 4-(methoxycarbonylmethoxy)-3-nitrophenol (6.0 g, 26.8 mmol), 1-(t-butyloxycarbonyl)-4-hydroxypiperidine (13.8 g, 68.9 mmol) and triphenylphosphine (18.0 g, 68.9 mmol) in tetrahydrofuran (80 mL) at 20° C. under argon was added diisopropyl azodicarboxylate (13.9 g, 68.9 mmol), dropwise over 0.75 h. The resulting solution was stirred at 20° C. for 4 h, then evaporated in vacuo. Chromatography of the residue on silica (400 g) eluting with 5–50% ether in hexane gave the title compound (10.1 g, 93%) as a yellow oil.

$^1$H NMR (CDCl$_3$) δ: 1.48 (9H, s), 1.65–2.00 (4H, m), 3.34 (2H, m), 3.69 (2H, m), 3.81 (3H, s), 4.44 (1H, m), 4.72 (2H, s), 7.02 (1H, d, J=9 Hz), 7.10 (1H, dd, J=9, 2 Hz), 7.43 (1H, d, J=2 Hz).

Description 23

6-(4-(N-(t-Butyloxycarbonyl)piperidinyl)oxy)-4H-benzo[1, 4]oxazin-3-one (D23)

A mixture of methyl 4-(4-(N-(t-butyloxycarbonyl)piperidinyl)oxy)-2-nitrophenoxyacetate (10.1 g, 24.6 mmol), 10% palladium on carbon (1.0 g) and methanol (300 mL) was hydrogenated at 20° C. and 1 bar for 4 h. Catalyst was removed by filtration and the filtrate was evaporated in vacuo to give an oily residue, which was dissolved in toluene. The resulting solution was heated at reflux for 2 h then evaporated in vacuo. Chromatography of the residue on silica with 25–100% ethyl acetate in hexane gave the title compound (7.2 g, 84%) as a colourless solid.

$^1$H NMR (CDCl$_3$) δ: 1.49 (9H, s), 1.74 (2H, m), 1.89 (2H, m), 3.02 (2H, m), 3.68 (2H, m), 4.34 (1H, m), 4.55 (2H, s), 6.44 (1H, d, J=2 Hz), 6.53 (1H, dd, J=9, 2 Hz), 6.89 (1H, d, J=9 Hz), 8.82 (1H, br s).

Description 24

6-(4-Piperidinyloxy)-4H-benzo[1,4]oxazin-3-one hydrochloride (D24)

A mixture of 6-(4-(N-(t-butyloxycarbonyl)piperidinyl)oxy)-4H-benzo[1,4]oxazin-3-one (3.78 g, 10.9 mmol), ethereal hydrogen chloride (50 mL) and dichloromethane (20 mL) was heated at 40° C. for 2 h, then allowed to stir at 20° C. for 18 h. The resulting colourless solid was collected by filtration to give the title compound (2.72 g, 88%).

$^1$H NMR (CD$_3$OD) δ: 1.95–2.25 (4H, m), 3.24 (2H, m), 3.40 (2H, m), 4.53 (2H, s), 4.60 (1H, m), 6.60 (1H, d, J=2 Hz), 6.65 (1H, dd, J=9, 2 Hz), 6.92 (1H, d, J=9 Hz).

Description 25

8-(4-Piperidinyloxy)-4H-benzo[1,4]oxazin-3-one hydrochloride (D25)

The title compound was prepared using analogous routes and intermediates to those used in the preparation of 6-(4-piperidinyloxy)-4H-benzo[1,4]oxazin-3-one, hydrochloride.

Description 26

7-Fluoro-5-hydroxy-2-methylquinoline Hydrobromide (D26)

Crotonaldehyde (28 mL, 0.33 mol) was added dropwise to a refluxing solution of 3,5-difluoroaniline (10.75 g, 0.083 mol) in 5 N hydrochloric acid (450 mL) and reflux was continued for a further 0.5 h. Reaction mixture was cooled, diluted with water (200 mL) and washed with ether (200 mL). The aqueous layer was basified (pH 14) with 50% NaOH (aq) and extracted into dichloromethane (3×200 mL). The combined organic phases were dried (Na$_2$SO$_4$) and evaporated in vacuo to give a dark oil which was purified by chromatography on silica gel (~100 g) with 50–100% ethyl acetate in hexane gradient elution to give 5,7-difluoro-2-methylquinoline as a brown solid (6.57 g, 44%). A mixture of 5,7-difluoro-2-methylquinoline (1.0 g, 5.6 mmol) and sodium methoxide (1.62 g, 30 mmol) in methanol (50 mL), was stirred at reflux for 18 h, cooled, and most of the methanol removed in vacuo. The residue was partitioned between ethyl acetate (100 mL), and water (100 mL). The organic phase was dried (Na$_2$SO$_4$) and evaporated in vacuo to give a brown oil which was purified by chromatography on silica gel (~60 g) with 20–30% ethyl acetate hexane gradient elution to give a yellow solid (0.57 g) which was suspended in 48% HBr (aq) (5 mL) and heated at reflux for 18 h. Reaction mixture was cooled and evaporated in vacuo to give the title compound as a brown solid (0.67 g, 46%).

Mass spectrum (API$^+$): Found 178 (MH$^+$). $C_{10}H_8FNO$ requires 177.

Description 27

5-(2-Bromoethoxy)-7-fluoro-2-methylquinoline (D27)

The title compound was prepared from 7-fluoro-5-hydroxy-2-methylquinoline hydrobromide and 1,2-dibromoethane using a similar procedure to Description 16, in 91% yield.

Description 28

8-Chloro-5-hydroxy-2-methylquinoline (D28)

Crotonaldehyde (17.5 mL, 0.21 mol) was added dropwise to a refluxing solution of 2-chloro-5-methoxyaniline hydrochloride (10.36 g, 53.4 mmol) in 5 N hydrochloric acid (450 mL) and reflux continued for a further 0.5 h. The reaction mixture was cooled and diluted with water (500 mL), then extracted with ether (400 mL). The aqueous layer was separated and basified using 50% aqueous NaOH (pH 14), and then extracted into dichloromethane (3×300 mL). The combined organic phases were dried ($Na_2SO_4$) and evaporated in vacuo to give a dark oil which was purified by chromatography on silica gel (~200 g) eluting with 20% ethyl acetate in hexane to give a brown oil (5.17 g) which was heated at reflux in a mixture of acetic acid (30 mL) and 48% hydrobromic acid (30 mL) for 66 h. Reaction mixture was evaporated in vacuo and the residue suspended in sat. $NaHCO_3$ (aq), then extracted into dichloromethane (3×50 mL). The combined organic phases were dried ($Na_2SO_4$) and evaporated in vacuo to give a brown solid (2.90 g, 28%).

Mass spectrum (API$^+$): Found 194 (MH$^+$). $C_{10}H_8{}^{35}ClNO$ requires 193.

Description 29

7-Chloro-5-hydroxy-2-methylquinoline (D29)

The title compound was prepared from 3-chloro-5-methoxyaniline using a similar procedure to Description 28, in 26% yield.

Mass spectrum (API$^+$): Found 194 (MH$^+$). $C_{10}H_8{}^{35}ClNO$ requires 193.

Description 30

5-(2-Bromoethoxy)-7-chloro-2-methylquinoline (D30)

The title compound was prepared from 7-chloro-5-hydroxy-2-methylquinoline and 1,2-dibromoethane using a similar procedure to Description 16.

Mass spectrum (API$^+$): Found 300 (MH$^+$). $C_{12}H_{11}{}^{79}Br^{35}ClNO$ requires 299.

EXAMPLE 1

8-{1-[2-(2-Methylquinolin-5-yloxy)ethyl]piperidin-4-yloxy}-4H-benzo[1,4]oxazin-3-one hydrochloride (E1).

The title compound was prepared by reaction of 8-(piperidin-4-yloxy)-4H-benzo[1,4]oxazin-3-one (0.225 g, 0.79 mmol), 5-(2-bromoethoxy)-2-methylquinoline (0.220 g, 0.83 mmol) and N,N-diisopropylethylamine (0.41 mL, 2.37 mmol) in isopropyl alcohol (15 mL). The mixture was heated at 90° C. with stirring for 124 h, then cooled and the isopropyl alcohol evaporated in vacuo. The residue was partitioned between dichloromethane (15 mL), and water (15 mL). The organic layer was added onto a 20 g prepacked silica column and eluted with 0–10% methanol in ethyl acetate. Fractions containing desired material were combined and evaporated in vacuo to give the title compound (0.24 g, 69%) as a colourless solid.

Mass spectrum (APCI$^+$): Found 434 (MH$^+$). $C_{25}H_{27}N_3O_4$ requires 433.

$^1$H NMR (250 MHz, CDCl$_3$) free base δ: 2.07–1.85 (m, 4H), 2.55–2.45 (m, 2H), 2.73 (s, 3H), 3.01–2.93 (m, 4H), 4.36–4.27 (m, 3H), 4.63 (s, 2H), 6.47 (dd, 1H), 6.66 (dd, 1H), 6.89–6.79 (m, 2H), 7.25 (d, 1H), 7.63–7.52 (m, 2H), 8.44 (d, 1H), 8.85 (s, 1H).

EXAMPLE 2

5-{2-[4-(3H-Benzimidazol-4-ylmethyl)piperazin-1-yl]ethoxy}-2-methylquinoline (E2).

A mixture of 2-methyl-5-(2-piperazin-1-ylethoxy)quinoline (0.04 g, 0.15 mmol) and 3H-benzimidazole-4-carboxaldehyde (0.024 g, 0.15 mmol) in 1,2-dichloroethane (5 mL) was treated with sodium triacetoxyborohydride (47 mg, 0.22 mmol) and stirred at 20° C. under an atmosphere of argon for 24 h. The mixture was then treated with saturated aqueous $NaHCO_3$ (20 mL) and the organic layer separated and purified directly by chromatography on silica (ethyl acetate to 10% methanol/ethyl acetate), to afford the title compound (0.013 g, 22%) as a solid.

Mass spectrum (APCI$^+$): Found 402 (MH$^+$). $C_{24}H_{27}N_5O$ requires 401.

EXAMPLE 3

5-{4-[2-(2-Methylquinolin-5-yloxy)ethyl]piperazin-1-ylmethyl}quinoline (E3).

The title compound was prepared using the method described in Example 2.

Mass spectrum (APCI$^+$): Found 413 (MH$^+$). $C_{26}H_{28}N_4O$ requires 412.

EXAMPLE 4

5-{4-[2-(2-Methylquinolin-5-yloxy)ethyl]piperazin-1-ylmethyl}quinoxaline (E4).

The title compound was prepared using the method described in Example 2.

Mass spectrum (APCI$^+$): Found 414 (MH$^+$). $C_{25}H_{27}N_5O$ requires 413.

EXAMPLE 5

8-{1-[2-(2-Methylquinolin-5-yloxy)ethyl]piperidin-4-ylmethyl}4H-benzo[1,4]oxazin-3-one (E5)

The title compound was prepared from 8-(piperidin-4-ylmethyl)-4H-benzo[1,4]oxazin-3-one and 5-(2-bromoethoxy)-2-methylquinoline in a similar manner to Example 1.

Mass spectrum (API$^+$): Found 432 (MH$^+$). $C_{26}H_{29}N_3O_3$ requires 431.

¹H NMR (CDCl₃) δ: 1.25–1.40 (2H, m), 1.50–1.70 (3H, m), 2.10–2.20 (2H, m), 2.57 (2H, d, J=7 Hz), 2.72 (3H, s), 2.93 (2H, t, J=7 Hz), 3.00–3.08 (2H, m), 4.27 (2H, t, J=6 Hz), 4.58 (2H, s), 6.63 (1H, d, J=8 Hz), 6.75–6.85 (2H, m), 6.87 (1H, t, J=8 Hz), 7.23 (1H, d, J=8 Hz), 7.50–7.64 (2H, m), 7.83 (1H, br. s), 8.42 (1H, d, J=8 Hz).

EXAMPLE 6

8-{1-[2-(7-Fluoro-2-methylquinolin-5-yloxy)ethyl]piperidin-4-ylmethyl}-4H-benzo[1,4]oxazin-3-one (E6)

The title compound was prepared from 8-piperidin-4-ylmethyl-4H-benzo[1,4]oxazin-3-one and 5-(2-bromoethoxy)-7-fluoro-2-methylquinoline in a similar manner to Example 1.

Mass spectrum (API⁺): Found 450 (MH⁺). $C_{26}H_{28}FN_3O_3$ requires 449.

¹H NMR (CDCl₃) δ: 1.25–1.40 (2H, m), 1.50–1.70 (3H, m), 2.10–2.20 (2H, m), 2.57 (2H, d, J=7 Hz), 2.70 (3H, s), 2.93 (2H, t, J=7 Hz), 3.00–3.08 (2H, m), 4.24 (2H, t, J=6 Hz), 4.58 (2H, s), 6.59 (1H, dd, J=8, 2Hz), 6.64 (1H, dd, J=8, 2 Hz), 6.80 (1H, d, J=8 Hz), 6.87 (1H, t, J=8 Hz), 7.18 (1H, d, J=8 Hz), 7.22 (1H, dd, J=10, 2 Hz), 7.80 (1H, br. s), 8.35 (1H, d, J=8 Hz).

EXAMPLE 7

8-{1-[2-(7-Chloro-2-methylquinolin-5-yloxy)ethyl]piperidin-4-ylmethyl}-4H-benzo[1,4]oxazin-3-one (E7)

The title compound was prepared from 8-(piperidin-4-ylmethyl)-4H-benzo[1,4]oxazin-3-one and 5-(2-bromoethoxy)-7-chloro-2-methylquinoline in a similar manner to Example 1.

Mass spectrum (API⁺): Found 466 (MH⁺). $C_{26}H_{28}^{35}ClN_3O_3$ requires 465.

¹H NMR (CDCl₃) δ: 1.25–1.41 (2H, m), 1.50–1.70 (3H, m), 2.10–2.20 (2H, m), 2.57 (2H, d, J=6 Hz), 2.70 (3H, s), 2.92 (2H, t, J=7 Hz), 3.00–3.06 (2H, m), 4.24 (2H, t, J=6 Hz), 4.58 (2H, s), 6.66 (1H, d, J=8 Hz), 6.73–6.85 (2H, m), 6.86 (1H, t, J=8 Hz), 7.21 (1H, d, J=8 Hz), 7.59 (1H, s), 8.34 (1H, d, J=8 Hz), 8.57 (1H, br. s).

EXAMPLE 8

8-{1-[2-(2-Methylquinazolin-5-yloxy)ethyl]piperidin-4-ylmethyl}-4H-benzo[1,4]oxazin-3-one (E8)

The title compound was prepared from 8-(piperidin-4-ylmethyl)-4H-benzo[1,4]oxazin-3-one and 5-(2-(methanesulphonyloxy)ethoxy)-2-methylquinazoline in a similar manner to Example 1.

Mass spectrum (API⁺): Found 433 (MH⁺). $C_{25}H_{28}N_4O_3$ requires 432. ¹H NMR (CDCl₃) δ: 1.25–1.40 (2H, m), 1.50–1.70 (3H, m), 2.10–2.20 (2H, m), 2.57 (2H, d, J=7 Hz), 2.88 (3H, s), 2.94 (2H, t, J=6 Hz), 3.00–3.06 (2H, m), 4.30 (2H, t, J=6 Hz), 4.58 (2H, s), 6.65 (1H, d, J=8 Hz), 6.75–6.95 (3H, m), 7.48 (1H, d, J=8 Hz), 7.74 (1H, t, J=8 Hz), 8.09 (1H, br. s), 9.63 (1H, s).

EXAMPLE 9

4-Methyl-8-{1-[2-(2-methylquinolin-5-yloxy)ethyl]piperidin-4-ylmethyl}-4H-benzo[1,4]oxazin-3-one (E9)

The title compound was prepared from 4-methyl-8-(piperidin-4-ylmethyl)4H-benzo[1,4]oxazin-3-one and 5-(2-bromoethoxy)-2-methylquinoline in a similar manner to Example 1.

Mass spectrum (API⁺): Found 446 (MH⁺). $C_{27}H_{31}N_3O_3$ requires 445.

¹H NMR (CDCl₃) δ: 1.25–1.40 (2H, m), 1.45–1.70 (3H, m), 2.10–2.20 (2H, m), 2.58 (2H, d, J=7 Hz), 2.72 (3H, s), 2.93 (2H, t, J=6 Hz), 3.00–3.08 (2H, m), 3.35 (3H, s), 4.27 (2H, t, J=6 Hz), 4.58 (2H, s), 6.79 (1H, d, J=8 Hz), 6.81 (2H, d, J=8 Hz), 6.96 (1H, t, J=7 Hz), 7.23 (1H, d, J=8 Hz), 7.50–7.70 (2H, m), 8.43 (1H, d, J=8 Hz).

EXAMPLE 10

8-{1-[2-(7-Fluoro-2-methylquinolin-5-yloxy)ethyl]piperidin-4-ylmethyl}-4-methyl-4H-benzo[1,4]oxazin-3-one (E10)

The title compound was prepared from 4-methyl-8-(piperidin-4-ylmethyl)-4H-benzo[1,4]oxazin-3-one and 5-(2-bromoethoxy)-7-fluoro-2-methylquinoline in a similar manner to Example 1.

Mass spectrum (API⁺): Found 464 (MH⁺). $C_{27}H_{30}FN_3O_3$ requires 463.

¹H NMR (CDCl₃) δ: 1.25–1.40 (2H, m), 1.50–1.70 (3H, m), 2.10–2.20 (2H, m), 2.58 (2H, d, J=7 Hz), 2.70 (3H, s), 2.92 (2H, t, J=7 Hz), 2.98–3.05 (2H, m), 3.35 (3H, s), 4.24 (2H, t, J=6 Hz), 4.58 (2H, s), 6.59 (1H, dd, J=8, 2Hz), 6.84 (2H, dd, J=8, 2 Hz), 6.96 (1H, t, J=8 Hz), 7.18 (1H, d, J=8 Hz), 7.23 (1H, dd, J=10,2 Hz), 8.35 (1H, d, J=8 Hz).

EXAMPLE 11

8-{1-[2-(7-Chloro-2-methylquinolin-5-yloxy)ethyl]piperidin-4-ylmethyl}-4-methyl-4H-benzo[1,4]oxazin-3-one (E1)

The title compound was prepared from 4-methyl-8-(piperidin-4-ylmethyl)-4H-benzo[1,4]oxazin-3-one and 5-(2-bromoethoxy)-7-chloro-2-methylquinoline in a similar manner to Example 1.

Mass spectrum (API⁺): Found 480 (MH⁺). $C_{27}H_{30}^{35}ClN_3O_3$ requires 479.

¹H NMR (CDCl₃) δ: 1.25–1.41 (2H, m), 1.50–1.70 (3H, m), 2.05–2.20 (2H, m), 2.58 (2H, d, J=6 Hz), 2.71 (3H, s), 2.92 (2H, t, J=6 Hz), 2.98–3.04 (2H, m), 3.35 (3H, s), 4.24 (2H, t, J=6 Hz), 4.58 (2H, s), 6.77 (1H, s), 6.85 (2H, d, J=8 Hz), 6.96 (1H, t, J=8 Hz), 7.22 (1H, d, J=8 Hz), 7.59 (1H, s), 8.34 (1H, d, J=8 Hz).

EXAMPLE 12

4-Methyl-8-{1-[2-(2-methylquinazolin-5-yloxy)ethyl]piperidin-4-ylmethyl}-4H-benzo[1,4]oxazin-3-one (E12)

The title compound was prepared from 4-methyl-8-(piperidin-4-ylmethyl)-4H-benzo[1,4]oxazin-3-one and 5-(2-(methanesulphonyloxy)ethoxy)-2-methylquinazoline in a similar manner to Example 1.

Mass spectrum (API⁺): Found 447 (MH⁺). $C_{26}H_{30}N_4O_3$ requires 446. ¹H NMR (CDCl₃) δ: 1.27–1.40 (2H, m), 1.50–1.70 (3H, m), 2.10–2.20 (2H, m), 2.58 (2H, d, J=7 Hz), 2.88 (3H, s), 2.94 (2H, t, J=6 Hz), 3.00–3.06 (2H, m), 3.36 (3H, s), 4.30 (2H, t, J=6 Hz), 4.58 (2H, s), 6.88 (3H, m), 6.96 (1H, t, J=8 Hz), 7.48 (1H, d, J=8 Hz), 7.74 (1H, t, J=8 Hz), 9.63 (1H, s).

The invention claimed is:

1. A compound of formula (I) or a pharmaceutically acceptable salt thereof:

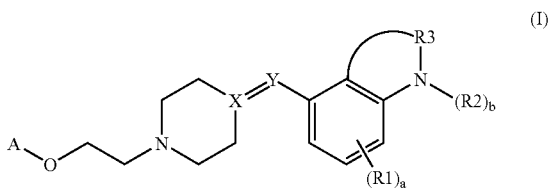

(I)

wherein:

A is phenyl, naphthyl, indolyl, quinolinyl, quinazolinyl, indazolyl, isoquinolinyl or benzofuranyl; any of which is optionally substituted by 1 to 4 substituents, which may be the same or different, and which are selected from the following group: halogen, hydroxy, cyano, $CF_3$, $C_{1-6}$alkyl, $C_{1-6}$alkoxy, $C_{1-6}$alkoxy$C_{1-6}$alkoxy$C_{1-6}$alkyl, $C_{3-7}$cycloalkyl$C_{1-6}$alkoxy, $C_{1-6}$alkanoyl, $C_{1-6}$alkylsulfonyl, $C_{1-6}$alkylsulfinyl, $C_{1-6}$alkylsulfonyloxy, $C_{1-6}$alkylsulfonyl$C_{1-6}$alkyl, $C_{1-6}$alkylsulfonamido, $C_{1-6}$alkylamido, $C_{1-6}$alkylsulfonamido$C_{1-6}$alkyl and $C_{1-6}$alkylamido$C_{1-6}$alkyl;

X is carbon, Y is CH and

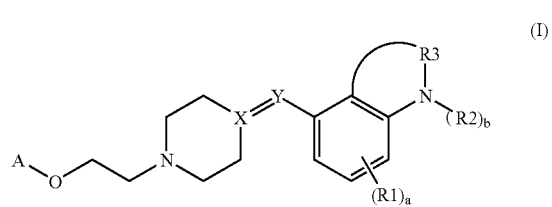

(I)

is a double bond; or X is CH, Y is CH₂ or oxygen and

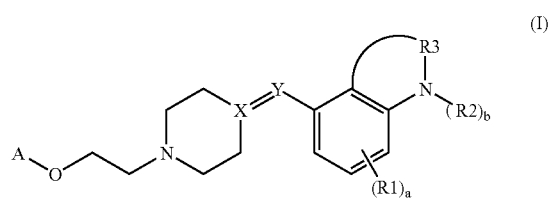

(I)

is a single bond; or X is nitrogen, Y is CH₂ and

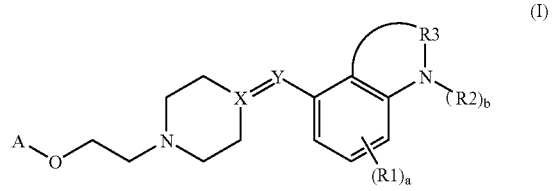

(I)

is a single bond;

R1 is halogen, cyano, or $C_{1-6}$alkoxy;

a is 0, 1, 2 or 3;

b is 0 or 1;

R2 is hydrogen, $C_{1-6}$alkyl, $C_{1-6}$alkanoyl, fluoro$C_{1-6}$alkanoyl, $C_{1-6}$alkylsulfonyl, fluoro$C_{1-6}$alkylsulfonyl, carbamoyl, $C_{1-6}$alkylcarbamoyl or aryl$C_{1-6}$alkyl; and R3, together with the nitrogen atom to which it is attached, forms an optionally substituted benzoxazinone, benzoimidazolyl, quinoxalinyl or quinolinyl group.

2. A compound as claimed in claim 1, wherein A is quinolinyl or quinazolinyl.

3. A compound as claimed in claim 2, wherein A is 5-(2-methyl)quinolinyl or 5-(2-methyl)quinazolinyl.

4. A compound as claimed in claim 1, wherein R1 is fluoro.

5. A compound as claimed in claim 1, wherein a is 0, 1 or 2.

6. A compound as claimed in claim 1, wherein when b is 1, R2 is hydrogen, $C_{1-6}$alkyl or $C_{1-6}$alkylsulfonyl.

7. A compound as claimed in claim 1 which is:

8-{1-[2-(2-Methylquinolin-5-yloxy)ethyl]piperidin-4-yloxy}-4H-benzo[1,4]oxazin-3-one hydrochloride;

5-{2-[4-(3 H-Benzimidazol-4-ylmethyl)piperazin-1-yl]ethoxy}-2-methylquinoline;

5-{4-[2-(2-Methylquinolin-5-yloxy)ethyl]piperazin-1-ylmethyl}quinoline;

5-{4-[2-(2-Methylquinolin-5-yloxy)ethyl]piperazin-1-ylmethyl}quinoxaline;

8-{1-[2-(2-Methylquinolin-5-yloxy)ethyl]piperidin-4-ylmethyl}4H-benzo [1,4]oxazin-3-one;

8-{1-[2-(7-Fluoro-2-methylquinolin-5-yloxy)ethyl]piperidin-4-ylmethyl}-4H-benzo[1,4]oxazin-3-one;

8-{1-[2-(7-Chloro-2-methylquinolin-5-yloxy)ethyl]piperidin-4-ylmethyl}-4H-benzo[1,4]oxazin-3-one;

8-{1-[2-(2-Methylquinazolin-5-yloxy)ethyl]piperidin-4-ylmethyl}-4H-benzo [1,4]oxazin-3-one;

4-Methyl-8-{1-[2-(2-methylquinolin-5-yloxy)ethyl]piperidin-4-ylmethyl}-4H-benzo[1,4]oxazin-3-one;

8-{1-[2-(7-Fluoro-2-methylquinolin-5-yloxy)ethyl]piperidin-4-ylmethyl}-4-methyl-4H-benzo[1,4]oxazin-3-one;

8-{1-[2-(7-Chloro-2-methylquinolin-5-yloxy)ethyl]piperidin-4-ylmethyl}-4-methyl-4H-benzo[1,4]oxazin-3-one;

4-Methyl-8-{1-[2-(2-methylquinazolin-5-yloxy)ethyl]piperidin-4-ylmethyl}-4H-benzo[1,4]oxazin-3-one;

or a pharmaceutically acceptable salt thereof.

8. A process for the preparation of the compound of formula (I) as claimed in claim 1 or a pharmaceutically acceptable salt thereof, which process comprises:

(a) the coupling of a compound of formula (II):

(II)

wherein A is as defined for formula (I) and L is a leaving group, with a compound of formula (III):

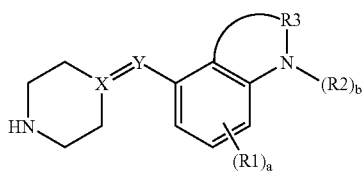
(III)

wherein a, b, R1, R2, R3, X, Y and

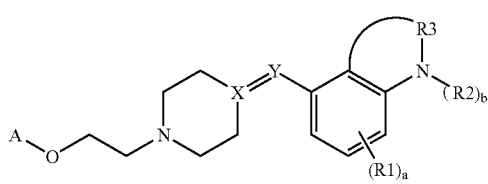
(I)

are as defined for formula (I);
or
(b) for a compound wherein X is nitrogen, the coupling of a compound of formula (IV):

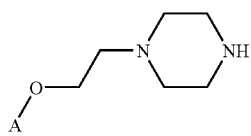
(IV)

wherein A is as defined for formula (I), with a compound of formula (V):

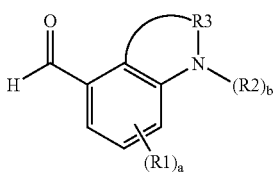
(V)

wherein a, b, R1, R2 and R3 are as defined for formula (I); and thereafter optionally for process (a) or process (b):
  removing any protecting groups and/or
  converting the compound of formula (I) into another compound of formula (I) or
  forming a pharmaceutically acceptable salt.

9. A pharmaceutical composition comprising the compound as claimed in claim 1 and a pharmaceutically acceptable diluent, carrier or excipient.

10. A process for preparing a pharmaceutical composition comprising mixing the compound according to claim 1 and a pharmaceutically acceptable carrier or excipient.

11. A method of treating depression or anxiety which comprises administering to a patient in need thereof a safe and therapeutically effective amount of the compound as defined in claim 1.

12. A method of treating depression or anxiety which comprises administering to a patient in need thereof a safe and therapeutically effective amount of the composition as defined in claim 9.

* * * * *